US008076479B2

(12) United States Patent
Chen et al.

(10) Patent No.: US 8,076,479 B2
(45) Date of Patent: *Dec. 13, 2011

(54) PROCESS AND INTERMEDIATES FOR THE SYNTHESIS OF (3-ALKYL-5-PIPERIDIN-1-YL-3,3A-DIHYDRO-PYRAZOLO[1,5-A]PYRIMIDIN-7-YL)-AMINO DERIVATIVES AND INTERMEDIATES

(75) Inventors: Frank Xing Chen, Plainsboro, NJ (US); Kartik M. Keertikar, East Windsor, NJ (US); Shen-Chun Kuo, Union, NJ (US); Hong-Chang Lee, Livingston, NJ (US); Ramani R. Raghavan, Kew Gardens, NY (US); George G. Wu, Basking Ridge, NJ (US); Ji Xie, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 1017 days.

This patent is subject to a terminal disclaimer.

(21) Appl. No.: 11/893,857

(22) Filed: Aug. 17, 2007

(65) Prior Publication Data

US 2008/0058518 A1 Mar. 6, 2008

Related U.S. Application Data

(60) Provisional application No. 60/840,648, filed on Aug. 28, 2006, provisional application No. 60/851,951, filed on Oct. 14, 2006.

(51) Int. Cl.
*C07D 487/04* (2006.01)
*A61K 31/519* (2006.01)

(52) U.S. Cl. ..................... 544/281; 514/259.3

(58) Field of Classification Search .................. 544/281
See application file for complete search history.

(56) References Cited

U.S. PATENT DOCUMENTS

| 7,119,200 | B2 | 10/2006 | Guzi et al. |
| 2004/0209878 | A1 | 10/2004 | Guzi et al. |
| 2004/0210060 | A1 | 10/2004 | Delplanche et al. |

OTHER PUBLICATIONS

Danilewics, J.C. et al., "Design of Selective Thrombin Inhibitors Based on the(R)-Phe-Pre-Arg Sequence", J. Med. Chem.; 2002; 45 (12) pp. 2432-2453.
Ekborg-Ott, K.H. et al., "Highly Enantioselective HPLC Separations Using the Covalently Bonded Macrocyclic Antibiotic, Ristocetin A, Chiral Stationary Phase", Chirality; 1998; 10; pp. 434-483.
Menche, D. at al., "Design, synthesis andn biological evaluation of novel analogues of archazolid; A highly potent simplified V-ATPase inhibitor"; Bioorganic and Medicinal Chemistry Letters; 2007; 17; pp. 1732-1735.
Morley, C. et al., "Complementary Enantioselective Approaches to the Quinolizidine Alkaloids Lupinine and Epilupinine by Elonate Claisen Rearrangements or Direct Allylation of Piperidin-2-ylacetuc Acid Derivatives", J. Chem Soc. Perkin Transactions I; 1994; 63, p. 2903-2907.
Toy, M.S. et al.; "d-and I-Polyconidine"; J. Am. Chem. Soc; 1960; 82; pp. 2613-2616.
International Search Report, PCT/US2007/018289; mailed Jan. 23, 2008; 3 pages.
International Search Report PCT/US2007/018305; mailed Jul. 15, 2009.
International Preliminary Report on Patentability; Written Opinion, PCT/US2007/018305; mailed Jul. 28, 2009, 12 pages.
International Preliminary Report on Patentability, Written Opinion, PCT/US2007/018289; mailed Aug. 18, 2006; 6 pages.

*Primary Examiner* — Susanna Moore
(74) *Attorney, Agent, or Firm* — Henry C. Jeanette; David A. Muthard

(57) ABSTRACT

Disclosed is a process for the synthesis of compounds of Formula I

Formula I

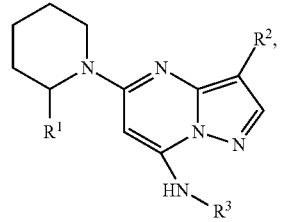

by sequentially aminating, first with a primary amine and then with a secondary amine, an intermediate compound of the structure of Formula E1,

E1

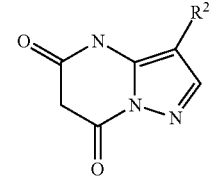

wherein $R^1$ is a linear, branched, or cyclic alkyloxy functional group of the structure ($-R^{2a}-OH$), $R^{2a}$ is a linear, branched or cyclic alkyl group, $R^2$ is a linear, branched or cyclic alkyl group, and $R^3$ is an alkylene-heterocycle, said process comprising forming intermediate compound of Formula E1 by reacting, in a refluxing reaction solvent selected from alcohols having 5 or less carbon atoms and mixtures of two or more thereof, a methanol solution of a salt of a 4-alkyl-3-amino-pyrazole compound of Formula C1, Formula C1

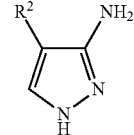

with a diamidization reagent selected from dimethylmalonate, monomethylmalonyl-chloride, and malonyl dichloride in the presence of a Lewis base having sufficient proton affinity to abstract a proton from the 1-position nitrogen on the pyrazole ring.

41 Claims, No Drawings

US 8,076,479 B2

PROCESS AND INTERMEDIATES FOR THE SYNTHESIS OF (3-ALKYL-5-PIPERIDIN-1-YL-3,3A-DIHYDRO-PYRAZOLO[1,5-A]PYRIMIDIN-7-YL)-AMINO DERIVATIVES AND INTERMEDIATES

CROSS-REFERENCE TO RELATED APPLICATIONS

The present application claims the priority of each of U.S. Provisional Application Nos. 60/840,648 filed Aug. 28, 2006, and 60/851,951 filed on Oct. 14, 2006 each of which is incorporated herein in its entirety by reference.

FIELD OF THE INVENTION

This application discloses a novel process to (3-alkyl-5-piperidin-1-yl-3,3a-dihydro-pyrazolo[1,5-a]pyrimidin-7-yl)-amino derivatives, which have utility, for example, as pharmaceutically active compounds, and intermediates useful in the synthesis thereof.

BACKGROUND OF THE INVENTION

Identification of any publication in this section or any section of this application is not an admission that such publication is prior art to the present invention.

As described in Published U.S. Patent Application No. 2004-0209878 A1, filed on Feb. 11, 2004 (the '878 publication), which is incorporated herein in its entirety, 3-alkyl-5-piperidin-1-yl-3,3a-dihydro-pyrazolo[1,5-a]pyrimidin-7-yl)-amino derivatives (as illustrated in Formula I, where $R^1$ is a linear, branched, or cyclic alkyloxy functional group of the structure ($-R^{2a}-OH$), $R^{2a}$ is a linear, branched or cyclic alkyl group, $R^2$ is a linear, branched or cyclic alkyl group, and $R^3$ is selected from alkylheterocycles, for example, 3-alkylene-pyridine-N-oxide, have activity as cyclin-dependent kinase inhibitor (CDK inhibitor) compounds.

Formula I

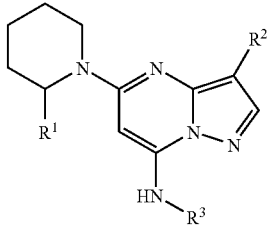

As described in the '878 publication, in these compounds can be prepared through the general routes described below in Scheme I.

Scheme I

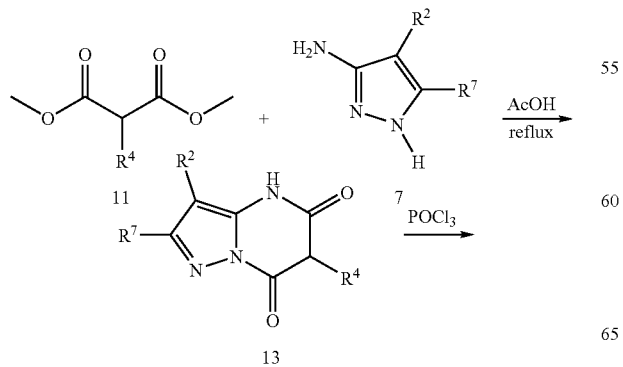

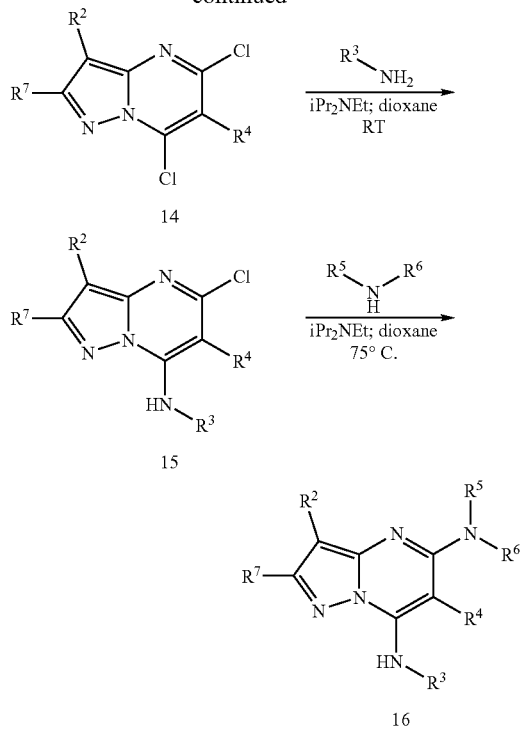

Where $R^1$, $R^2$, and $R^3$ are as defined above, $R^4$ and $R^7$ are selected from H and $R^2$, and $R^5$ and $R^6$ are taken together to form an alkyl heterocycle, for example, pyrimidin-1-yl, optionally substituted on any carbon with a linear, branched, or cyclic alkyl, which is optionally substituted with hydroxide. Accordingly, a dicarboxylic acid diester (compound 11, a malonate diester or an appropriately substituted malonate diester derivative where R4 is other than hydrogen) is condensed with pyrazole compound (7) by refluxing in acetic acid, forming a pyridone compound (13). The pyridone compound is subsequently derivatized by dehalogenation it, for example, by treatment with the chlorinating reagent $POCl_3$ to provide the dichloride derivative. The dihalogen derivative (14) is then sequentially treated with amines to provide the amino-functionalized CDK inhibitor product 16, wherein R5 and R6 are taken together to form an alkyl heterocycle, for example, pyrimidin-1-yl, and wherein "R" (Scheme 1) is a linear, branched, or cyclic alkyl, optionally substituted with pyridine N-oxide.

One example of these inhibitors is the compound of Formula II.

Formula II

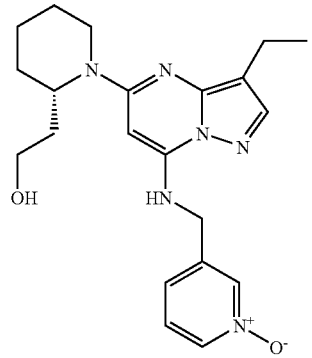

The synthesis of the compound of Formula II is described in the '878 publication according to Scheme II:

Scheme II:

Step 1—Amidization to Form Substituted Pyrazole

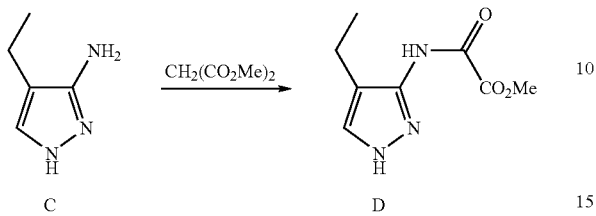

Step 2—Formation and Dehalogenation of pyrazolo[1,5a] pyrimidine

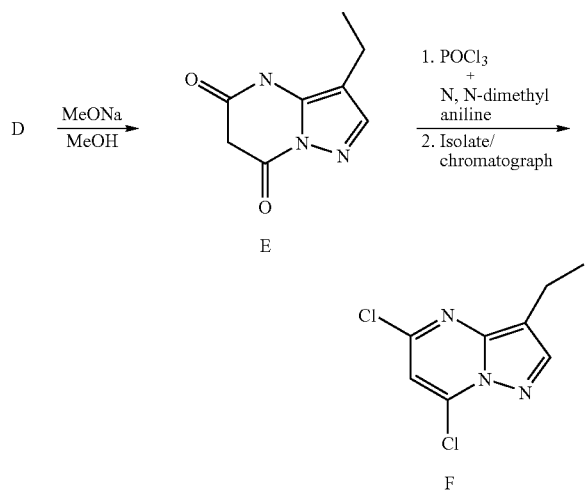

Step 3—Amination (Two Separate, Sequential Reactions)

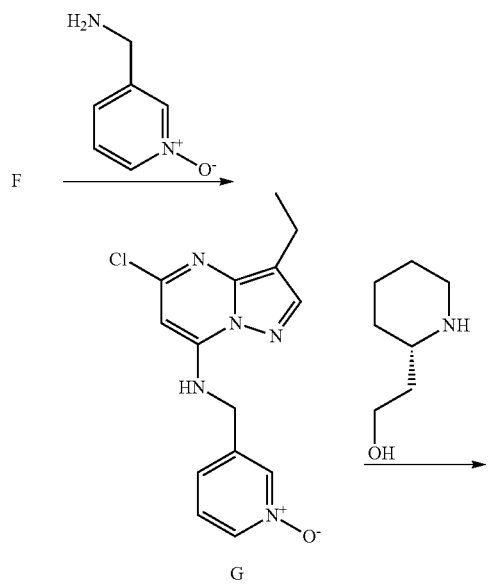

-continued

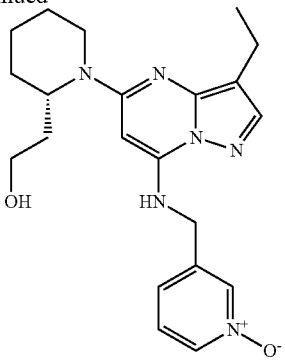

Formula II

As described in the '878 publication, Synthetic Scheme II leading to the compound of Formula II has several disadvantages from the standpoint of commercial scale synthesis. In step 1, the starting material (compound "C") used in the formation of compound "D" is a sticky, viscous oil which is difficult to process (weigh, transfer, and blend). Moreover, step 1, as described in the '878 publication, requires isolation and chromatographic purification of compounds C and D prior to carrying out each subsequent derivatization reaction. In addition, as described in the '878 publication, the reaction of compound C with malonate diester is carried out using the diester as a solvent. After isolation and purification of the resultant malonate adduct, compound D, ring closure to form diketone compound E is carried out in methanol. In accordance with the procedure described in the '878 publication, compound E is isolated and dried, then converted to the corresponding dichloride in N,N-dimethyl aniline by treatment with phosphorous oxychloride ($POCl_3$). The dichloride thus formed was isolated and purified by chromatography prior to the sequential amination reactions. Additionally, the compounds of Formula G and of Formula II require chromatography purification and isolations, as described in the '878 publication.

As further described in the '878 publication, each of the amination reactions were run separately with isolation and chromatographic purification between amination reactions. Accordingly, the '878 publication describes the preparation of the compound of Formula II utilizing a scheme consisting of five separate reaction steps with intervening isolation and purification of the products, each sequential step being carried out in a different solvent system. The overall yield of the compound of Formula II reported for this synthesis, based on starting compound C (Scheme II) is about 20%.

OBJECTIVES AND SUMMARY OF THE INVENTION

In view of the foregoing, what is needed is a synthetic scheme useful for preparing the CDK inhibitor compounds of interest utilizing fewer reaction steps. Moreover, what is needed is a synthetic scheme for the preparation of CDK inhibiting compounds of Formula I with a higher product yield based on compound C starting material consumed. Moreover, what is needed is a process which minimizes the need for chromatographic purification of intermediates, and utilizes fewer changes of solvent systems. In addition, what is needed is a synthesis scheme for compounds of Formula I which is amenable for scale-up to a batch size suitable for commercial scale preparation. These and other objectives and/or advantages are provided by the present invention.

One aspect of the present invention is a process for the synthesis of CDK inhibitor compounds having the structure of Formula I

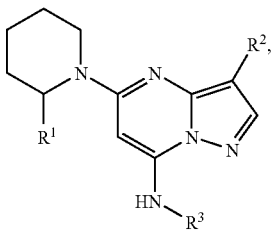

Formula I from an intermediate pyrazolo[1,5-a]pyrimidine-5,7 dione compound of the structure of Formula E1,

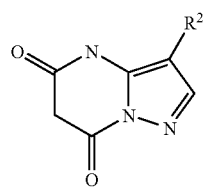

E1 wherein $R^1$ is a linear, branched, or cyclic alkyloxy functional group of the structure (—$R^{2a}$—OH), $R^{2a}$ is a linear, branched or cyclic alkyl group, $R^2$ is a linear, branched or cyclic alkyl group, and $R^3$ is an alkylene-heterocycle, preferably, 3-alkylene-pyridine-N-oxide, said process comprising: (a) forming the intermediate compound of the structure of Formula E1 by reacting, in a refluxing reaction solvent selected from alcohols having 5 or less carbon atoms and mixtures of two or more thereof, a methanol solution of a salt of a 4-alkyl-3-amino-pyrazole compound of Formula C1,

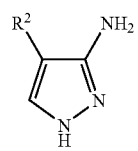

Formula C1 with a diamidization reagent selected from dimethylmalonate, monomethylmalonylchloride, and malonyl dichloride in the presence of a Lewis base having sufficient proton affinity to abstract a proton from the 1-position nitrogen on the pyrazole ring; (b) derivatizing the intermediate E1 prepared in Step (a) to provide the compound of Formula F1,

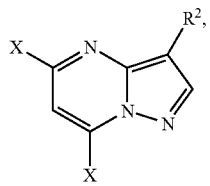

Formula F1 wherein "X" is selected from chloride, bromide, iodide, fluoride, and a sulfonyl group; and (c) sequentially aminating the compound of Formula F1, in sub-step (ci) with a primary amine, substituting the X-group on the 7-carbon atom of the pyrazolo-pyridine moiety, and in sub-step (cii) with a secondary amine replacing the "X"-group residing on the 5-carbon atom of the pyrazolo-pyridine moiety, wherein the structure of the amine used in each sub-step is independently selected to provide a suitable substituent to form the compound of Formula 1.

In some embodiments of the invention, in Step (a), preferably the counter ion of the salt of the compound of Formula C1 is selected from oxalate, tosylate, and chloride, more preferably the counter ion is oxalate. In some embodiments of the invention, $R^2$ is a linear alkyl group of 4 carbons or less, preferably $R^2$ is ethyl, thus the compound of Formula E1 is a compound of Formula E

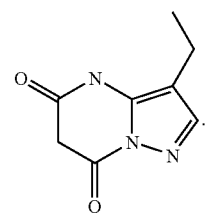

Formula E

In some embodiments of the invention the reaction solvent is preferably selected from methanol and ethanol, more preferably methanol. In some embodiments it is preferred for the Lewis base to be selected from metal alkoxide bases, more preferably the base is selected from lithium, sodium and potassium alkoxide bases, more preferably the Lewis base is selected from sodium ethoxide and sodium methoxide, and more preferably the Lewis base is sodium methoxide.

In some embodiments of the present invention, Step (b) is carried out by providing a solution of the compound of Formula E1 and halogenating the compound of Formula E1 by treating the solution containing the compound of Formula E1 with a halogenating agent in the presence of a base, providing a compound of the structure of F1,

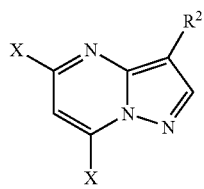

Formula F1 where "X" is a halogen selected from chloride, bromide, iodide and fluoride. Preferably the solution is made by dissolving the compound of Formula E1 in a solvent selected from acetonitrile and toluene, more preferably the solution comprises toluene.

When the "X" substituent of the compound of Formula F1 is a halogen, preferably it is chloride. When the "X" substituent of the compound of Formula F1 is chloride, the halogenating agent used in Step "b" is a chlorinating agent preferably selected from phosphorous oxychloride, phosphorous pentachloride, and thionyl chloride, more preferably the halogenating agent is phosphorous oxychloride. When a chlorinating agent is used in Step "b", preferably the base used is selected from dimethyl aniline, pyridine, diisopropylethylamine, and triethyl amine, more preferably dimethyl aniline.

In some embodiments of the present invention, Step (b) is carried out by providing a solution of the compound of Formula E1 and sulfonating the compound of Formula E1 by treating the solution containing the compound of Formula E1 with a sulfonating agent in the presence of a base, providing a compound of the structure of F1 (shown above) where "X" is a sulfonyl group, preferably selected from aryl sulfonyl and methyl sulfonyl, more preferably methyl sulfonyl chloride. In some embodiments in which Step (c) comprises a sulfonation reaction, preferably the sulfonating agent is methyl sulfonyl chloride. Preferably the solution is made by dissolving the compound of Formula E1 in a solvent selected from acetonitrile and toluene, more preferably the solution comprises toluene.

In some embodiments of the invention which include forming the compound of the structure of Formula E1 and halogenating the compound of Formula E1 in Step "b", preferably $R^2$ is ethyl, thus, the compound of the structure of F1 is a compound of the structure of Formula F

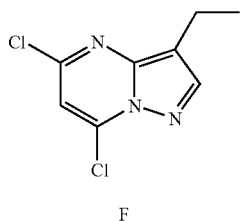

Formula F

In some embodiments of the present invention process, the compound of the "X" substituents in the compound of Formula F1 are chloride, and sub-step (ci), aminating the compound of Formula F1 with a primary amine, comprises: (a) adding a water and a base, preferably $K_3PO_4$, either separately or as an aqueous solution, to the product mixture from derivatizing Step "b" which contains the dihalide compound of the structure of Formula F1; and (ii) reacting a primary amine, or a salt thereof, with the mixture under refluxing conditions to form the compound of the structure of Formula Ga,

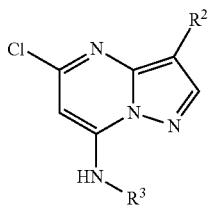

Formula Ga wherein $R^2$ and $R^3$ are as defined above.

In some embodiments it is preferred for the primary amine used in reacting Step "c (ii)" to be the primary amine salt of the structure of Formula F1a,

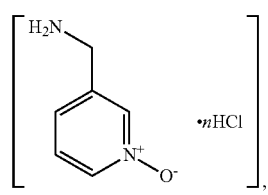

Formula F1a wherein "n"=1 or 2, preferably 2, the reaction thereby forming a compound having the structure of Formula G1,

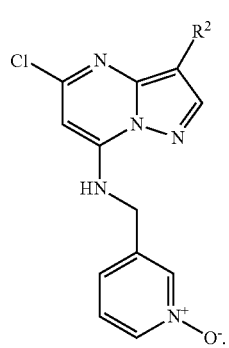

Formula G1

In some embodiments it is preferred for an amount of water to be added to the reaction mixture in amination sub-Step (ci) which is sufficient to provide a volumetric ratio of acetonitrile:water in the reaction mixture of about 1:5.

In some embodiments where the "X" substituent is chloride, amination sub-Step (cii) comprises refluxing the isolated compound of Formula Ga prepared in first amination sub-Step (ci) in N-methylpyrollidine with a secondary amine in the presence of sodium carbonate and sufficient water to maintain a refluxing temperature of from about 140° C. to about 160° C., thereby yielding the compound of Formula I.

In some preferred embodiments, the compound of Formula Ga prepared in first amination sub-Step (ci) is the compound of Formula G1, and the secondary amine used in second amination sub-Step (cii) is an amine of the structure of Formula Ha

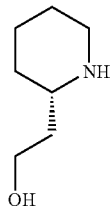

Ha thereby providing the compound of Formula Ia

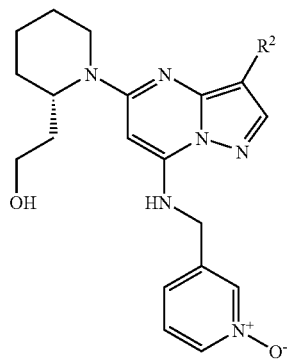

Formula Ia

In some preferred embodiments, $R^2$ is ethyl, thus the compound of the structure of Formula G1 is compound G, and the compound of Formula I prepared in Step e is the compound of Formula II.

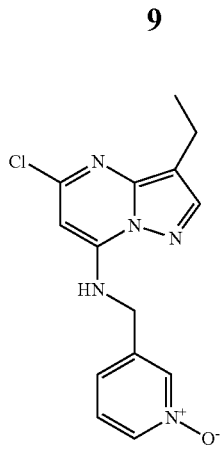
Formula G

In one embodiment, the present invention is a process for making Cyclin-Dependent Kinase inhibitor compounds (CDK inhibitor) of Formula II,

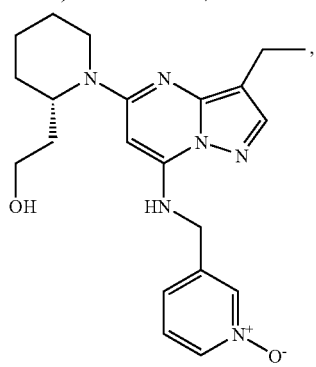
Formula II the process comprising:
(a) reacting a refluxing solution comprising one or more of an alcohol having 5 carbons or less and a salt of the 4-ethyl-1H-pyrazol-3-ylamine compound of Formula C

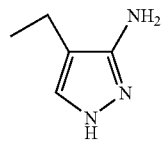
Formula C with an amidization reagent selected from dimethylmalonate, monomethylmalonylchloride, and malonyl dichloride in the presence of an metal alkoxide base comprising an alkoxide moiety having 5 carbon atoms or less to form the product having the structure of Formula E,

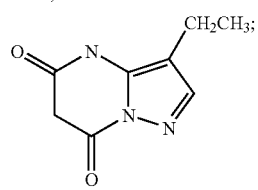
E (b) halogenating the isolated product of Formula E from reacting Step "a" by treating an acetonitrile solution containing the compound of Formula E isolated from Step "a" with phosphorous oxychloride in the presence of N,N-dimethylaniline to form a compound of the structure of F;

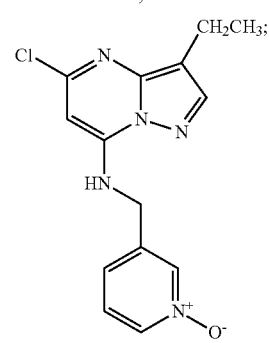
Formula F (c) refluxing the dichloride of Formula F prepared in Step "b" in the presence of a hydrochloride salt of pyridin-3-yl-methylamine-1-oxide, a base selected from potassium carbonate and potassium phosphate tribasic ($K_3PO_4$), and a reaction medium selected from acetonitrile and an acetonitrile/water mixture to form the compound of Formula G,

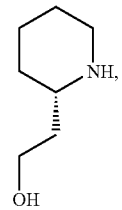
Formula G (d) reacting the isolated compound of Formula G prepared in refluxing Step "c" with the amino alcohol compound structure of G1a,

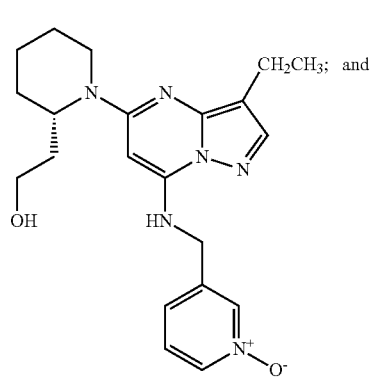
G1a by refluxing the compound of Formula G in N-methylpyrrollidine in the presence of sodium carbonate and sufficient water to maintain a reaction temperature of from about 140° C. to about 160° C., thereby yielding the compound of Formula II, Formula II (e) optionally isolating the compound of Formula II prepared in refluxing Step "d" from the reaction mixture by precipitating it with an anti-solvent;
(f) optionally recrystalling the isolated solids.

In some embodiments of the invention, the salt of the compound of Formula C in reacting Step "a" is selected from oxalate, tosylate, and chloride salts, preferably the oxalate salt. In some embodiments the solvent in reacting Step "a" is preferably selected from methanol and ethanol. In some embodiments the metal alkoxide base in reacting Step "a" is preferably selected from sodium methoxide and sodium ethoxide.

In some embodiments preferably the Lewis base used in Step "b" is preferably selected from N,N-dimethyl aniline, pyridine, diisopropylethylamine, and triethyl amine, more preferably N,N-dimethylaniline.

In some embodiments it is preferred for the refluxing solvent employed in step "c" to comprise a ratio of 5:1 water: acetonitrile. In some embodiments, the base used in Step "c" is preferably potassium phosphate tribasic. In some embodiments the salt of pyridin-3-yl-methylamine-1-oxide used in the reaction is the dihydrochloride salt.

In some embodiments the base used in Step "d" is selected from sodium carbonate and sodium bicarbonate, preferably the base used is sodium carbonate. In some embodiments it is preferred for an amount of water to be added to the reaction mixture in refluxing Step "d" sufficient to provide a volumetric ratio of N-methylpyrollidine:water in the reaction mixture of about 100:1.

In some embodiments using optional isolating step "e", it is preferred to use ethyl acetate to precipitate the solids. In some embodiments including optional recyrstallization step "f" it is preferred to use ethyl alcohol as a recrystallization solvent.

DETAILED DESCRIPTION OF THE INVENTION

As mentioned above, and described in the '009 publication, compounds of Formula I (as defined herein) are believed to have promising activity as useful pharmaceutical compounds having CDK inhibitor properties. The synthesis of these compounds, for example, the compound of Formula II, is described in detail in published U.S. Patent Application No. 2004-0209878 A1, filed on Feb. 11, 2004 (the '878 publication). The process for providing the compound of Formula II is described in the '878 application in Examples 507 to 508, 509, 1000 and 1001. These examples, as well as the entirety of the '878 application are incorporated herein by reference. As described above, and with reference to Schemes I and II, the preparation of these compounds in general proceeds through amidization of a pyrazole-3-yl-amine intermediate (eg, compound 7 of Scheme 1 above) with a malonate or malonate derivative, for example, a malonate diester, a malonate monoester acid chloride, or a malonate monoester acid, which is followed by cyclization to form the corresponding pyrazolo[1,5-a]pyrimidine-5,7-dione (for example, compound 13 in Scheme 1). Subsequent halogenation at the ketone sites (e.g. compound 14) followed by stepwise amination of the halide sites (e.g. compounds 15 and 16) yields the desired CDK inhibitor compounds.

The process of the present invention provides improvements in this general synthetic scheme by either adapting this process to either improve the yield of the product in some of these steps, combining two or more of these steps into a one-pot synthetic scheme, or alterations in the reaction scheme and methodology which leads to the provision of an intermediate or product as an easily isolated precipitate which obviates the need for chromatographic purification required in the previously described processes. Accordingly, each and severally the steps of the process of the present invention comprise an improved synthesis for the preparation of pyrazolo[1,5-a]pyrimidine compounds over those synthetic processes described in the '878 publication for preparation of pyrazolo-[1,5-a]-pyrimidine compounds. It will be appreciated that each and severally the improvements of the present invention can be incorporated into the previously described synthetic process to provide an improved synthetic process for the preparation of compounds with CDK inhibiting properties. Each improved step is described next.

One aspect of the present invention is an improved process for the provision of 5,7-dichloro-pyrazolo[1,5-a]pyrimidine compounds comprising an improved process for the preparation of intermediate compounds having the structure of Formula E1,

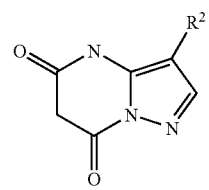

E1 wherein $R^2$ is a linear, branched or cyclic alkyl group, and its subsequent halogenation, or alternatively, its subsequent sulfonation, carried out in accordance with Scheme III.

Scheme III

Step 1—Formation of a pyrazolo[1,5-a]pyrimidine-5,7 dione:

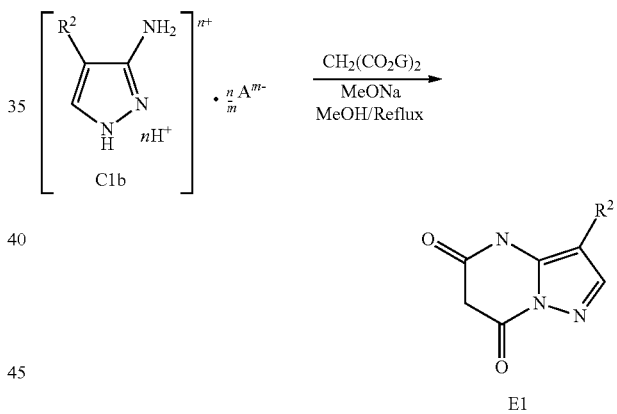

E1 where $R^2$ is a linear, branched or cyclic alkyl group, "$A^-$" is an anion of a carboxylic acid selected from oxalate, tosylate, and chloride, "n" is 1 or 2, "m" is the charge of the anion, and is either 1 or 2 depending upon the anion species, and "G" is selected independently for each occurrence from a methyl group and chloride, Step 2a—Formation of dihalide from the pyrazolo[1,5-a]pyrimidine-5,7-dione:

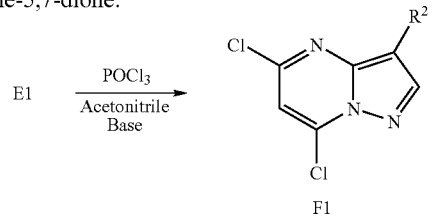

F1 where $R^2$ is defined above, or,

Step 2b—Formation of disulfonyl from the pyrazolo[1,5-a]pyrimidine-5,7-dione:

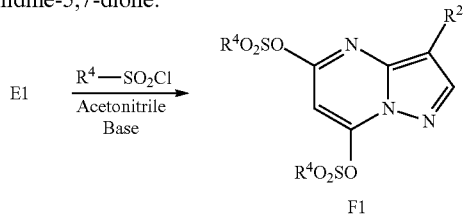

where $R^2$ is as defined above and $R^4$ is selected from a methyl group and an aryl group.

Amidation/Cyclization "One-Pot" Reaction

With regard to Scheme III, Step 1, the inventors have surprisingly found that a "one-pot" reaction can be carried out between salts of 4-alkyl-pyrazol-3-yl-amine (C1b) compounds and a malonic acid amidization reagent selected from dimethyl malonate (both "G" substituents are methyl), monomethylmalonylchloride (one "G" substituent is methyl and the other is chloride), and malonyldichloride (both "G" substituents are chloride) in the presence of a Lewis base having sufficient proton affinity to abstract a proton from the 1-position nitrogen on the pyrazole ring, yielding a corresponding malonamic acid methyl ester adducts. Under the conditions of the reaction, these adducts cyclize in situ to produce the corresponding pyrazolo[1,5-a]pyrimidine diketone (E1). As will be appreciated, for compound C1b, various acid salts can be employed and both mono-acid and diacid salts can be employed. Thus, for example, the acid salt can be prepared from oxalic acid, p-tolylsulfonic acid, or hydrochloric acid such that in the corresponding salt "A" is oxalate, tosylate, and chloride, respectively. Moreover, both monoacid and diacid salts can be prepared (thus "n" is 1 or 2 respectively). Both the monoacid and the diacid species can be prepared from either monoanionic species (for example, p-tolylsulfonate, thus "m" is 1) or dianionic species (for example, oxalate, thus "m" is 2). In general these salts can be prepared by treating a solution of the free base with the corresponding acid, for example, oxalic acid, tolysulfonic acid and hydrochloric acid, to precipitate, respectively, the corresponding oxalate, tosylate, and chloride salt. In general, the oxalate salt is preferred in the reaction of Scheme III.

Moreover, the inventors have found that conversion of the pyrazole-3yl-amine free base compound to a salt selected from oxalate, tosylate, and chloride prior to running the reaction also provides a reagent having advantageous handling properties. The corresponding pyrazole-3yl-amine free base compound is a viscous oil with a high affinity for metal surfaces. This aspect of this step of the invention facilitates scale-up of the reaction to a scale suitable for commercial production using ordinary production equipment and techniques.

Step 1 of reaction Scheme III utilizes a refluxing solvent comprising an alcohol of 5 carbon atoms or less. Preferably the reaction solvent is selected from ethanol and methanol, more preferably, methanol. As will be appreciated, depending upon the refluxing temperature desired the reaction mixture can comprise any alcohol of 5 carbon atoms or less and mixtures of two or more thereof, for example, isopropanyl. Other non-alcohol solvents can be employed so long as the reactants are soluble in them and they reflux at a suitable temperature, for example acetonitrile and tetrahydrofuran (THF). In general the reaction mixture is refluxed until chromatographic measurements indicate that the reaction is complete, as indicated by less than about 5% of the starting pyrazole compound remains unreacted. Under the above-described reaction condition the reaction typically requires about 10 hours of refluxing. Preferably reagents and reaction conditions are selected to complete the reaction in a period of from about 10 hours to about 20 hours.

The amidization/cyclization reaction of Scheme III is driven by a Lewis base having sufficient proton affinity to abstract a proton from the 1-position nitrogen of the pyrazole ring.

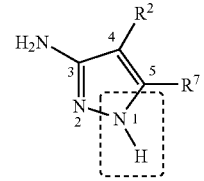

Suitable Lewis bases include metal alkoxide bases, for example, sodium, lithium, and potassium alkoxides, wherein the alkoxide portion of the complex is selected from linear, branched, and cyclic alkoxides having 6 carbon atoms or less. In general it is preferred to use sodium alkoxides selected from sodium methoxide and sodium ethoxide, which sodium methoxide being preferred because of its commercial availability.

It will be appreciated that other Lewis bases can also be employed, for example, diisopropylethyl amine (DIEA), triethyl amine (TEA), potassium phosphate tribasic, 1,8 diazabicyclo[5,4-0]undec-7-ene (DBU), and 4-dimethyl aminopyridine (DMAP).

The method of the present invention presented in Scheme III provides an additional advantage in that at the end of the reaction, quenching the reaction mixture with water and adjusting the pH of the mixture to a pH of from about pH 2 to about pH 5, preferably pH 3, precipitates the product pyrazolo-pyrimidine diketone product (13), which can be quantitatively recovered by filtration, thus eliminating the chromatographic purification at the intermediate and final stages necessary in the previous process. In general the pH can be adjusted by addition of amounts of HCl or NaOH as needed to bring the pH of the reaction mixture within the desired range.

It has been surprisingly found that by using methanol as a solvent with sodium methoxide and the oxalate salt of the 4-alkyl-pyrazole-3-yl-amine (C1c),

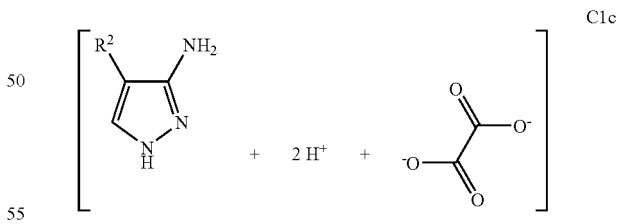

the corresponding diketone is produced in a yield of from about 80% to about 90%, based on starting pyrazole compound. When compared with a typical yield obtained from the diketone preparation described in the '878 publication, an increase in diketone yield of at least about 40% based on starting pyrazole compound is observed.

Diketone Derivitization—Halogenation of Diketone

The inventors have been the first to recognize that by employing the procedure illustrated in Step 1 of Scheme III the diketone intermediate can be provided as a precipitate which can be isolated by vacuum filtration for use in conversion to the corresponding dihalide, thus eliminating isolation of the amide intermediate and purification by chromatography to provide the ketone. In accordance with Scheme III, once obtained, preferably the precipitated diketone is isolated by vacuum filtration and dissolved in a suitable solvent for conversion into the dihalide. Suitable solvents include toluene, tetrahydrofuran (THF), and acetonitrile, with acetonitrile being the preferred solvent. Preferably, after redissolving the diketone, as shown in Scheme III, the diketone is converted into the dichloride by refluxing a solution containing the diketone with phosphorous oxychloride in the presence of a suitable base, for example, N,N-dimethylaniline, triethylamine, pyridine, and isopropyldiethylamine. It will be appreciated that other bases can be utilized.

It will be appreciated that the diketone provided by step 1 of the Scheme III process can be isolated for use in other reactions, for example, other halogenation reactions and sulfonylation reactions to provide an intermediate which can be further transformed in accordance with the processes described in the above-mentioned '878 publication, and thereby provide desirable CDK inhibitor compounds.

Once the dichloride compound F1 is obtained in accordance with Scheme III, combining the reaction mixture with water will precipitate the dichloride compound. Accordingly, the dichloride may be obtained in a form suitable for amination either as described below or in accordance with the above-mentioned '878 publication.

Diketone Derivitization—Diketone Sulfonylation

It will be appreciated that the diketone provided by step 1 of the Scheme III process can be converted to a disulfonyl compound of Formula F1 (above) wherein the "X" substituent has the formula "RSO2O—", wherein R=Aryl or Methyl. A sulfonyl intermediate of this formula can be used to provide a compound of Formula II using amination reactions described below in the same manner as they are carried out using the above-described halogenated intermediates, for example, the dichloride of Formula F. Sulfonylation can be accomplished by treating the diketone with a suitable sulfonyl chloride in the presence of a base, as for the halogenation reaction described above. Preferably, the sulfonyl chloride is selected from methylsulfonylchloride and an arylsulfonylchloride.

First Amination Reaction

Although it will be appreciated that the compound of the formula F1 prepared by the inventive process can be employed to prepare compounds of Formula I utilizing previously described amination reactions, the inventors have surprising found that utilizing a primary amine salt in the first amination reaction provides process improvements. Accordingly, the inventors have surprisingly found that treating an the acetonitrile solution of the pyrazolo-pyrimidine dihalide compound (the compound of Formula F1, wherein the "X" substituent is a halogen), prepared as described above, with potassium phosphate tribasic and water in the presence of a primary amine salt, there is precipitated from the reaction mixture a first amine adduct in a form suitable for use directly in a second amination reaction (described herein below).

Accordingly, for example, a dichloride or sulfonyl obtained as a precipitate from Scheme III, Step 2a or 2b, described above, can be dried and employed in a first amination reaction in accordance with Scheme IV (illustrated with the dichloride).

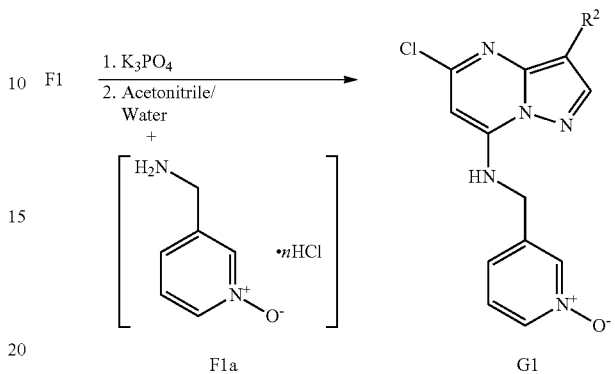

Scheme IV wherein "n"=1 or 2, preferably 2, and $R^2$ is as defined herein.

Thus, the dichloride F1 is dissolved in Acetonitrile, which solution is mixed with a base, preferably a base selected from potassium carbonate and potassium phosphate tribasic, more preferably potassium phosphate tribasic ($K_3PO_4$) and a sufficient amount of water (preferably 1:5 by volume, Acetonitrile:water) to promote the amination reaction under refluxing conditions. As shown in Scheme IV, either the mono hydrochloride salt ("n"=1) or the dihydrochloride salt ("n"=2), can be employed, preferably the dihydrochloride salt of the desired amine is used. The dihydrochloride salt is available as an article of commerce, for example, from Daito Chemix Corporation, Osaka, Japan. The salt can also be preprepared by treating the amine with a suitable acid to precipitate the salt.

Although it is preferred to use tripotassium phosphate (potassium phosphate, tribasic) in the amination reaction, it will be appreciated that other bases can be employed, for example, sodium carbonate and sodium bicarbonate. Although the amount of water used in promoting the reaction is not critical, the inventors have surprisingly found that a ratio of 1:5 by volume of acetonitrile:water permits the amination reaction to run to completion (determined by chromatography when less than about 5% of the starting material remains unreacted) in a period of about 6 hours, as compared to the reaction run under the conditions described in the '878 publication (no-water present) which requires nearly 72 hours to complete. Typically by selecting an appropriate ratio of water the reaction can be run to completion in a period of from about 4 hours to about 10 hours. The reaction conditions of the present invention also boost the yield of first amine adduct by about 10%, and provide the product in a suitable form for use in the subsequent second amination reaction (described below) directly without the need for chromatography to isolate and purify the product. Optionally, the purity of the product can be increased by reslurrying the product in an acetonitrile/water mixture.

Second Amination Reaction

In some embodiments of the present invention, the pyrazolo[1,5-a]pyridine-7yl-amine adduct of Formula G1, prepared in accordance with Scheme IV, is further derivatized by amination at the 5-chloro position in accordance with Scheme V.

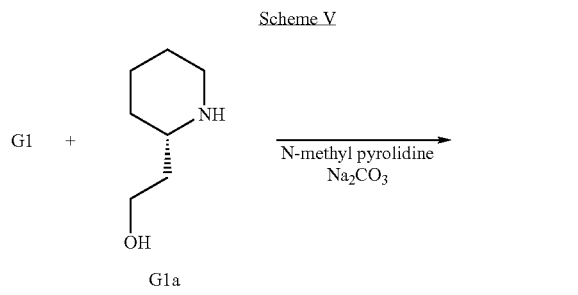

The inventors have surprisingly found that the second amination reaction can be carried out in refluxing N-methylpyrrolidine (NMP) in the presence of sodium carbonate and a small amount of water, where it is preferred to provide an amount of water in the system sufficient to maintain a refluxing temperature of from about 140° C. to about 160° C. For example, when the solvent in which the refluxing step is carried out is NMP, it is sufficient to maintain water at a level of about 0.1 M in the solvent to provide the desired refluxing temperature. Depending upon the refluxing equipment, however, it may be necessary to add an amount of water that is up to about 0.5× the volume of solvent employed to carry out the refluxing step.

The inventors have surprisingly discovered that too little water leads to the formation of a high level of impurities in the reaction product which impedes separation of the product from the reaction mixture. The inventors have also found that when too much water is present in the reaction mixture it can slow the reaction rate, requiring undesirably long reaction times. Accordingly, it is desirable to maintain an amount of water in the reaction mixture that permits reflux in the temperature range of from about 120° C. to about 180° C., more preferably about 140° C. to about 160° C., and most preferably a refluxing temperature of about 150° C.

The solvent in which the second amination reaction is carried out is preferably NMP, however, this step may be carried out in other high boiling solvents, for example, N,N-dimethylaniline, dimethylsulfoxide (DMSO), phenyl ether, dimethylformamide (DMF), di(ethyleneglycolmethyl)ether, and anisole. If a sufficient amount of the secondary amine amination reagent is employed (with reference to Scheme V, for example, the amino-alcohol compound G1a), it can serve also as the solvent for the second amination step. In general, the solvent employed in the second amination step is used in an amount up to 10× the volume of the aminating reagent, but preferably an amount of from about 1× the volume of the aminating reagent to about 2× the volume of the aminating reagent is employed, preferably about 1.5× the volume of the aminating reagent.

The amount of base used is preferably up to about 2× (mole) the amount of chloride substrate which is to be aminated (compound of Formula "G"), more preferably from about 0.2× mole to about 1× mole amount, and more preferably the base is present in an amount about 2× mole relative to the amount of chloride substrate used.

Although $R^2$ in the above-described synthetic procedures can comprise any linear, branched, or cyclic alkyl substituent, it is preferred for $R^2$ to be a linear alkyl substituent of four carbons or fewer, and more preferably, $R^2$ is an ethyl substituent ($-CH_2-CH_3$).

Crystallization

Typically, the second amination reaction is considered completed when from about 90% to about 95% of the starting chloride substrate has been consumed. Once the second amination reaction is run to completion (90-95% consumption) the inventors have surprisingly found that the product (compound of Formula H1) can optionally be isolated directly from the reaction mixture by quenching the reaction of Scheme V with water and extracting the mixture with ethyl acetate. Typically, the reaction is quenched with an amount of water based on the reaction mixture volume. After extracting the product from the reaction mixture, the ethyl acetate extract is concentrated under vacuum, following which the product is precipitated from the concentrate by adding a mixture of ethyl acetate and THF to the concentrate as an antisolvent to promote crystallization and subsequent precipitation of the desired product. The precipitated product is sufficiently pure that column chromatography is not needed to isolate or purify the product. Optionally, however, additional purity can be achieved by recrystallizing the precipitated product from ethanol or a mixture of t-butylmethyl ether and ethanol. Using this method, typically isolated yields obtained are of from about 50% to about 70% based on the amount of second amine adduct prepared in the reaction of Scheme V.

As mentioned above, while the above-described synthetic methods can each and severally be used alone or in combination and integrated into synthetic procedures described in the '878 publication for the preparation of any of the compounds of Formula I, and thereby render improvements and advantages in the synthetic procedure, it is believed that each of the improvements of the present invention synthesis will be most applicable when used together in the provision of the compound of Formula II in accordance with the synthetic procedure schematically illustrated in Scheme VI.

Scheme VI

Step 1—Diketone Synthesis

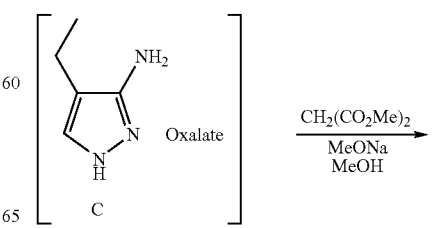

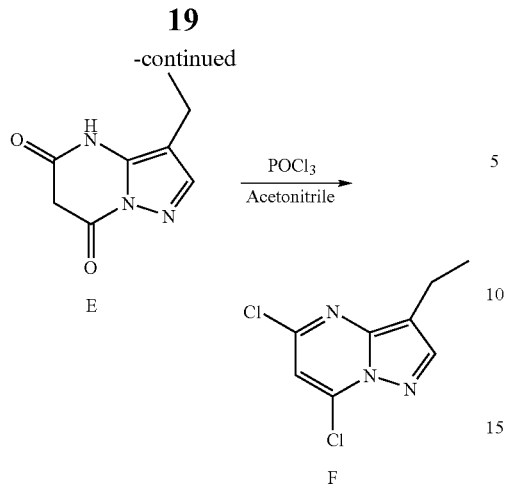

E

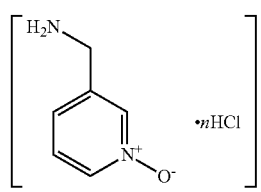

F

Step 2—First Amination Using Primary Amine

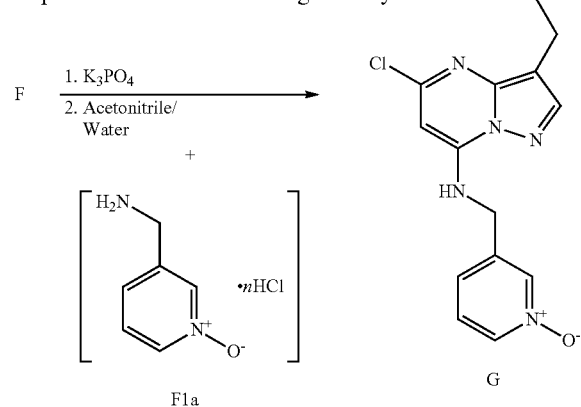

wherein "n"=1 or 2, preferably 2

Step 3—Second Amidation with Secondary Amine

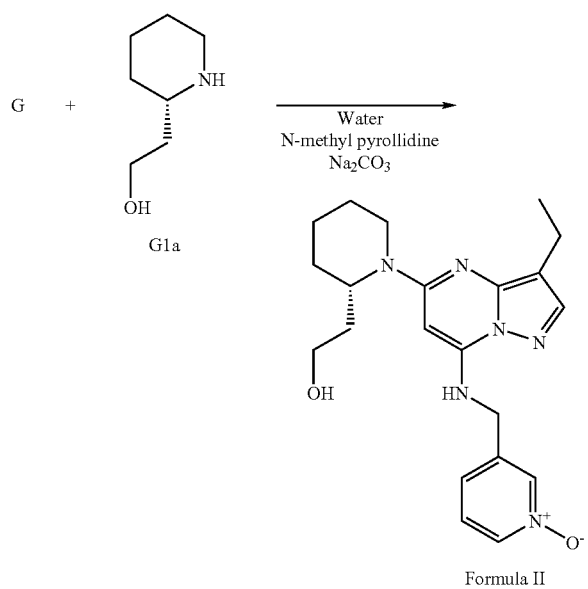

Formula II

Accordingly, in Step 1, diketone E is provided by reacting a methanol solution of the oxalate salt of starting pyrazole "C" with dimethyl malonate in the presence of sodium methoxide under refluxing conditions as described above. Thereafter, the dichloride compound "F" is formed from the isolated diketone compound "E" prepared in Step 1 by treatment of the diketone with phosphorous oxychloride in acetonitrile in accordance with the procedures described above. In Step 2, the isolated dichloride compound "F" is converted to a first amine adduct by amination in refluxing acetonitrile/water in the presence of $K_3PO_4$ and the compound of Formula F1a,

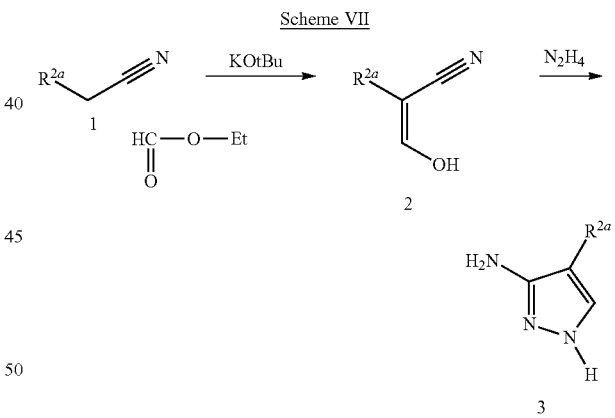

Formula F1a, where "n"=1 or 2, under refluxing conditions in accordance with the procedures described above. Preferably, the dihydrochloride salt of Formula F1a is employed, thus "n"=2. In Step 3 of Scheme VI, the isolated first amine adduct compound "G" is converted to the second amine adduct by treatment with 2-piperidin-2-yl-ethanol (compound "G1a") in the presence of sodium carbonate and a trace of water in refluxing N-methylpyrrolidinone in accordance with the procedures described above to yield the compound of Formula II.

There follows a general description of the provision of various starting materials which may be useful in the above-described synthetic schemes.

As described in the '878 publication, the aminopyrazole compounds used in the synthesis of the present invention can be made in accordance with the following Scheme VII.

Thus, treatment of a starting nitrile with potassium t-butoxide and ethyl formate gives rise to the intermediate enol 2 which upon treatment with hydrazine gives the desired substituted 3-aminopyrazole.

The malonate diesters used in the synthesis are commercially available, for example, dimethyl malonate from Aldrich, or can be prepared from the reaction of alcohol and the appropriate malonic acid derivative, for example, malonic acid chloride available from Aldrich, in accordance with known esterification reactions, for example, those disclosed in Organic Chemistry, $3^{rd}$ edition by Morrison and Boyd, Allyn and Bacon 1976.

The aminopyrazine N-oxide used in the reactions of the present invention can be prepared in accordance with the '878 publication, as described in Examples 198 through 203, which are incorporated herein by reference, can be used to prepare the aminopyridine N-oxide salt used in the first amination reaction, shown below in Scheme VIII.

Scheme VIII

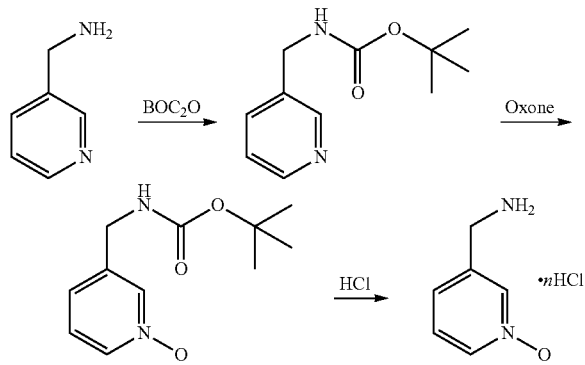

Accordingly, to a solution of 3-aminomethylpyridine (1.41 mL, 13.87 mmol) in CH$_2$Cl$_2$ (50 mL) was added BOC$_2$O (3.3 g, 1.1 eq.) and TEA with stirring at room temperature, the amino group is protected in step 1. Following this the reaction mixture was diluted with H$_2$O (50 mL) and extracted with CH$_2$Cl$_2$. The combined organics were dried over Na$_2$SO$_4$, filtered and concentrated under reduced pressure. The crude product was purified by flash chromatography using a 5% (10% NH$_4$OH in MeOH) solution in CH$_2$Cl$_2$ as eluent to give a yellow oil (2.66 g, 92% yield). LCMS: MH$^+$=209. Following this, a solution comprising the protected 3-aminopyridine compound and NaHCO$_3$ (21.8 g, 2.0 eq.) in MeOH (200 mL) and H$_2$O (250 mL) was prepared. A solution of oxone (58.6 g) in H$_2$O (250 mL) was added dropwise to amino-pyridine solution. The mixture was stirred at room temperature overnight, diluted with CH$_2$Cl$_2$ (500 mL) and filtered. The layers were separated and the aqueous layer extracted with CH$_2$Cl$_2$. The combined organics were dried over Na$_2$SO$_4$, filtered, and concentrated under reduced pressure to give a white solid (2.1 g, 72% yield). MS: MH$^+$=255.

In the last step, the protected amino-N-oxide compound was stirred at room temperature in 4M HCl in dioxane (0.97 mL) 2 hours to provide 3-amino-methyl-pyridine-N-oxide-hydrochlorides. LCMS: MH$^+$=125. The dihydrochloride salt is also available as an article of commerce, as described above.

The stereoisomer of the 2-Piperidin-2-yl-ethanol (Compound G1a) used in the second amination reaction may be prepared as described in the '878 publication in accordance with preparative Example 500, which is incorporated herein by reference in its entirety.

Compound G1a

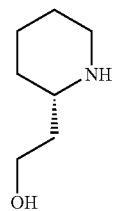

Accordingly, the S-isomer can be prepared from a mixture of R and S enantiomers of piperidine-2-ethanol (127 g, 980 mmol) in 95% EtOH (260 mL) was added to (S)-(+)-camphorsulfonic acid (228.7 g, 1.0 eq.) in 95% EtOH (150 mL) and the resulting solution was warmed to reflux. To the warm solution was added Et$_2$O (600 mL) and the solution cooled to room temperature and let stand 3 days. The resulting crystals were filtered and dried in vacuo (25 g): mp 173-173° C. (lit. 168° C.). The salt was then dissolved in NaOH (3M, 100 mL) and stirred 2 hours and the resulting solution was extracted with CH$_2$Cl$_2$ (5×100 mL). The combined organics were dried over Na$_2$SO$_4$, filtered, filtered and concentrated under reduced pressure to give (S)-piperidine-2-ethanol (7.8 g) a portion of which was recrystallized from Et$_2$O: mp=69-70° C. (lit. 68-69° C.); [α]$_D$=14.09 ® (CHCl$_3$, c=0.2).

The R-isomer of 2-Piperidin-2-yl-ethanol (Compound G1b) can be prepared by essentially the same procedure set forth above for the S-isomer but substituting (R)-(−)-camphorsulfonic acid. Accordingly, (R)-piperidine-2-ethanol was prepared. (1.27 g): [α]$_D$=11.3° (CHCl$_3$, c=0.2).

Compound G1b

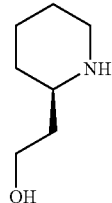

EXAMPLES

The reagents and solvents used in the examples are articles of commerce which, unless otherwise noted, were used as received. Completion of a reaction step is generally taken to be when 90% to 95% of the substrate used has been consumed, generally as determined by chromatography methods.

Example 1

Preparation of Diketone Compound E (Scheme VI)
3-Ethylpyrazolo[1,5-a]pyrimidine-5,7(4H,6H)-dione

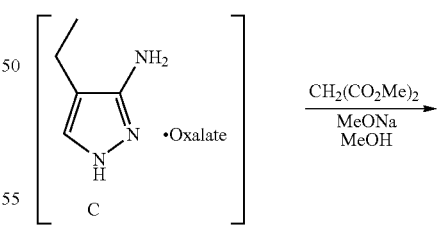

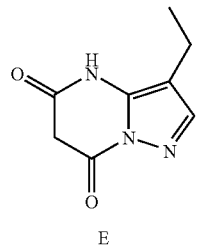

E 3-amino-4-ethylpyrazole oxalate (10 g, 50 mmole), dimethylmalonate (10 ml, 88 mmole), methyl alcohol (80 ml) and sodium methoxide (50 ml, 245 mmole, 25% in methyl alcohol). The batch was heated at reflux for 16 hours then cooled to room temperature. Celite (5 g) and water (60 ml) were added to the batch and agitated for 10 minutes. The batch was filtered to remove the solid residue. The filtrate was pH adjusted to pH~3 with aqueous HCl (10 ml) to effect precipitation. The precipitate (compound "E") was filtered and washed with water (40 ml). The wet cake was dried for 18 hours in vacuum oven maintained in the range of oven at 45° C. to 55° C., to give a solid product (84.3%, 7.5 g). $C_8H_9N_3O_3$, Mp: 200-205° C.; NMR in DMSO-d6: 1.05 (t, 3H), 2.23 (q, 2H), 3.26 (bs, 1H), 3.89 (bs, 1H), 7.61 (s, 1H), 11.50(bs, 1H).

Example 2

Preparation of Dichloride Compound F (Scheme VI) 5,7-Dichloro-3-Ethylpyrazolo[1,5-a]pyrimidine

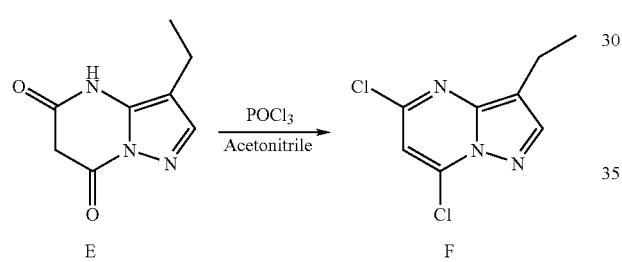

Into a 3-neck flask fitted with an inert gas inlet, a reflux condenser and a mechanical stirring apparatus and containing 83 liters of acetonitrile was placed 3-Ethylpyrazolo[1,5-a]pyrimidine-5,7(4H,6H)-dione (E) prepared as described in Step 1 (11.0 kg, 61.5 mole), N,N-dimethylaniline (8.0 L, 63 mole) and $POCl_3$ (7 kg, 430 mole). With stirring the mixture was brought to reflux and maintained under refluxing conditions for 15 hours. The reaction mixture was sampled periodically to monitor the amount of compound "E" present. After the conversion was complete, the solution was cooled to 15° C. Into the cooled reaction mixture was added water which had been cooled to a temperature of less than 20° C. The product is filtered and washed with 4 aliquots of acetonitrile-water (1:3) which had been cooled to a temperature of 20° C. followed by a wash with 10× water. The wet cake is dried in a vacuum oven maintained at 40° C. for at least 15 hours to yield the compound "F" (86.7%); $^1H$ NMR ($CDCl_3$): 1.32(t, 3H), 2.81 (q, 2H), 6.92 (s, 1H), 8.10 (s, 1H)

mp: 90-95° C.

Example 3

Preparation of Compound G (Scheme VI) 5-Chloro-3-Ethyl-N-[(1-oxido-pyridinyl)methyl]pyrazolo-[1,5-a]pyrimidine-5.7(4H,6H)-dion-7-amine Into a 3-liter, three-necked flask equipped with a thermometer, a reflux condenser and mechanical stirrer was charged an aliquot of the dichloride compound "F" prepared in Step 2 (150 g, 0.69 mole), potassium phosphate tribasic monohydrate (338.0 g, 1.47 mole), the dihydrochloride salt of N-oxide-pyridin-3-yl-methylamine, compound F1a (142.5 g, 0.72 mole), water (1500 ml) and acetonitrile (300 ml). The batch was heated at reflux for 6 hours. At the end of the refluxing period the batch was cooled to room temperature over 2 hours and then held at room temperature for 4 hours. The resulting precipitate was filtered and washed with water (600 ml). The wet cake was returned to the flask with water (1500 ml) and acetonitrile (300 ml), and heated to reflux. Reflux was maintained for 6 hours additional. At the end of the second reflux period the reaction mixture was cooled to room temperature over a 2 hour period and left to stand at room temperature for 4 hours. The resulting precipitate was filtered and washed with water (600 ml). The wet cake was dried in an air draft oven at 50° C. for 18 hours to give the first amine adduct "G" material (179 g, 84.9%). mp: 187-189C; NMR in CDCl3, 1.26(t, 3H), 2.73(q, 2H), 4.60(d, 2H), 5.87(s, 1H), 6.83(bs, 1H), 7.33(t, 1H), 7.70(d, 1H), 7.84(s, 1H), 8.58(d, 1H), 8.64 (d, 1H).

Example 4

Preparation of the Compound of Formula II (Scheme VI) 1-[3-Ethyl-7-[(1-oxido-3-pyridinyl)methyl]amino]pyrazolo[1,5-a]pyrimidin-5-yl]-2(s)-piperidinemethanol

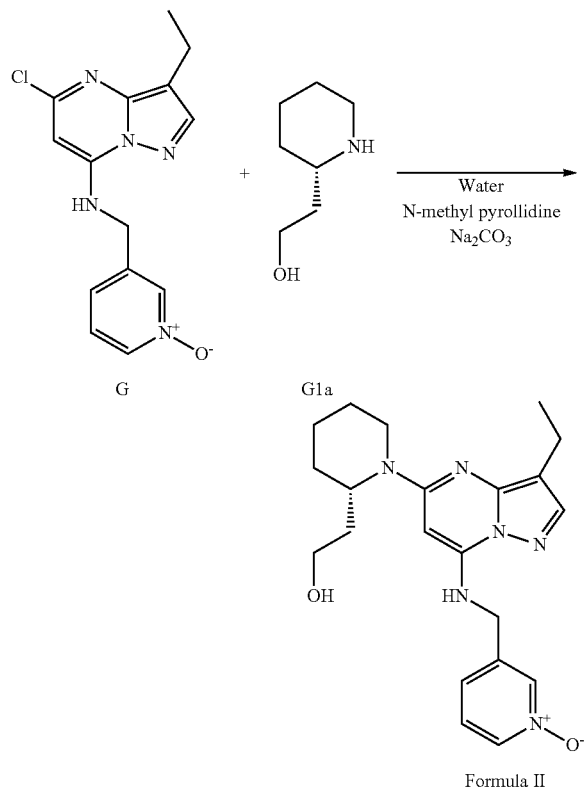

Into a three-neck flask fitted with a mechanical stirrer and a reflux condenser were placed the first amine adduct prepared in Step 3, compound "G", (7 kg, 23 mole), aminoalcohol compound G1a (5.6 kg, 43.3 mole), sodium carbonate (3.5 kg, 33.0 mole), 110 ml of water and 1-methyl-2-pyrrolidinone (NMP) (11 L). The reaction mixture was heated to 150° C. for 4 days. After chromatography indicated that the reaction was complete (90-95% substrate consumed), the reaction mixture was cooled to room temperature and quenched by adding water. The mixture was then extracted with ethyl acetate. The batch was dried by distillation of the water azeotrope under atmospheric pressure and concentrated to about 28 L volume. THF was added and the solution was heated to reflux until all the solids dissolve. Ethyl acetate and trietylamine are added to the hot solution. The batch was cooled to ambient and then agitated with the temperature maintained in the range of from 20° C. to 25° C. for 12 hours. The solids were collected by filtration, washed first with ethyl acetate then water, and dried in the filter under vacuum for 24 hours with the temperature maintained at from 40° C. to 50° C., yielding 4.9 kg, 51.3% of the compound of Formula II. DSC, 168.6° C.; Specific Rotation (10 mg/ml in MeOH, 20° C.), −117.8 °; $^1$HNMR (400 MHz, DMSO): 8.31 ppm (1H, s), 8.11-8.13 ppm (1H, td, J=5.7 Hz, J=1.4 Hz), 7.97 ppm (1H, t, J=6.7 Hz), 7.68 ppm (1H, s), 7.41 ppm (1H, s), 7.37-7.43 ppm (1H, dd), 5.55 ppm (1H, s), 4.85 ppm (1H, t, J=5.4 Hz), 4.49-4.59 ppm (3H, m), 4.24-4.28 ppm (1H, broad), 3.27-3.46 ppm (2H, m), 2.76-2.83 ppm (1H, t, J=13.0 Hz), 2.45-2.50 ppm (2H, q, J=7.5 Hz), 1.72-1.79 (1H, m), 1.54-1.68 ppm (6H, m), 1.30-1.34 ppm (1H, m), 1.16 ppm (3H, t, J=7.5 Hz)

The above description of the invention is intended to be illustrative and not limiting. Various changes or modifications in the embodiments described herein may occur to those skilled in the art. These changes can be made without departing from the scope or spirit of the invention

What is claimed is:

1. A process for the synthesis of CDK inhibitor compounds having the structure of Formula I

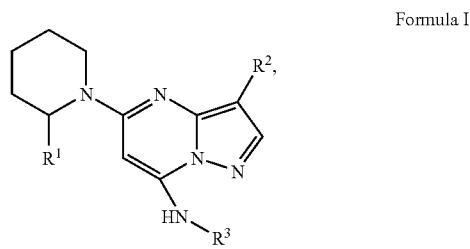

Formula I from an intermediate compound of the structure of Formula E1,

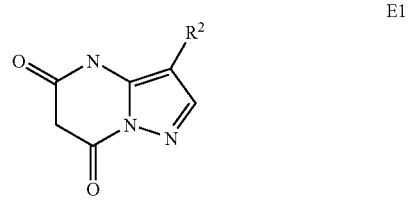

E1 wherein $R^1$ is a linear, branched, or cyclic alkyloxy functional group of the structure (—$R^{2a}$—OH), $R^{2a}$ is a linear, branched or cyclic alkyl group, $R^2$ is a linear, branched or cyclic alkyl group, and $R^3$ is an alkylene-heterocycle, said process comprising: (a) forming intermediate compound of Formula E1 by reacting, in a refluxing reaction solvent selected from the group consisting of alcohols having 5 or less carbon atoms and mixtures of two or more thereof, a methanol solution of a salt of a 4-alkyl-3-amino-pyrazole compound of Formula C1,

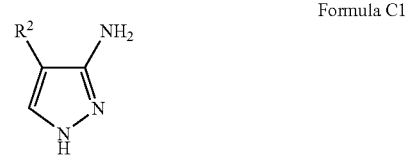

Formula C1 with a diamidization reagent selected from the group consisting of dimethylmalonate, monomethylmalonylchloride, and malonyl dichloride in the presence of a Lewis base having sufficient proton affinity to abstract a proton from the 1-position nitrogen on the pyrazole ring; (b) derivatizing the intermediate E1 prepared in Step (a) to provide the compound of Formula F1,

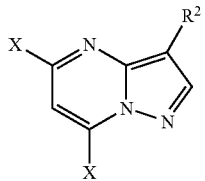

Formula F1 wherein "X" is selected from the group consisting of chloride, bromide, iodide, fluoride, and a sulfonyl group; and (c) sequentially aminating the compound of Formula F1 with a primary amine, and then with a secondary amine, to form the compound of Formula 1.

2. The process of claim 1 wherein, the salt of the compound of Formula C1 is selected from the group consisting of oxalate, tosylate, and chloride salt.

3. The process of claim 2 wherein, the salt of the compound of Formula C1 is an oxalate salt.

4. The process of claim 2 wherein, $R^2$ is a linear alkyl group of 4 carbons or less.

5. The process of claim 4 wherein, $R^2$ is ethyl.

6. The process of claim 4 wherein, the reaction solvent is selected from the group consisting of methanol and ethanol.

7. The process of claim 6 wherein the reaction solvent is methanol.

8. The process of claim 1 wherein, the Lewis base is selected from the group consisting of metal alkoxide bases.

9. The process of claim 4 wherein, the Lewis base is selected from the group consisting of metal alkoxide bases.

10. The process of claim 9 wherein, the Lewis base is selected from the group consisting of lithium, sodium and potassium alkoxide bases.

11. The process of claim 10 wherein, the Lewis base is selected from the group consisting of sodium ethoxide and sodium methoxide.

12. The process of claim 10 wherein, the Lewis base is sodium methoxide.

13. The process of claim 1 wherein, $R^3$ is 3-alkylene-pyridine-N-oxide.

14. The process of claim 9 wherein the process further comprises reacting the compound of Formula E1 to provide a compound of the structure of Formula F1,

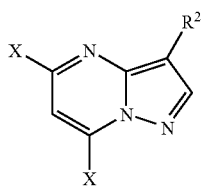

Formula F1 where "X" is selected from the group consisting of chloride, bromide, iodide, fluoride and a sulfonyl group having the structure $R^4$—$SO_2$—, wherein $R^4$ is selected from the group consisting of methyl and aryl, said reaction comprising:
a) providing the compound of Formula E1 in an acetonitrile solution; and
b) derivatizing the compound of Formula E1 by treating the acetonitrile solution containing the compound of Formula E1 from Step "b" with a reagent selected from the group consisting of a halogenating agent and a sulfonating agent in the presence of a base selected from the group consisting of dimethyl aniline, pyridine, diisopropylethylamine, and triethyl amine.

15. The process of claim 14 wherein, the reagent selected in derivatizing step (b) is a chlorinating agent selected from the group consisting of phosphorous oxychloride, phosphorous pentachloride, and thionyl chloride.

16. The process of claim 15 wherein, the chlorinating agent is phosphorous oxychloride.

17. The process of claim 14 wherein the reagent selected in derivatizing step (b) is a sulfonating agent selected from the group consisting of arylsulfonylchloride and methylsulfonylchloride.

18. The process of claim 17 wherein said sulfonating agent is methylsulfonylchloride.

19. The process of claim 14 wherein, the base is dimethyl aniline.

20. The process of claim 1, wherein said sequential amination of the compound of Formula F1 comprises forming the compound of Formula F1 from the compound of Formula E1,

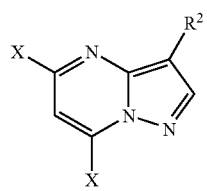

Formula F1 wherein $R^2$ is a linear, branched or cyclic alkyl group and "X" is selected from the group consisting of chloride, bromide, iodide, fluoride and a sulfonyl group having the structure $R^4$—$SO_2$—, and forming therefrom a compound of the structure of Formula Ga5,

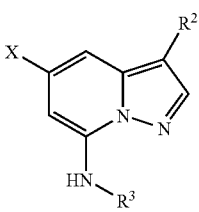

Formula Ga5 wherein, X and $R^2$ are as defined above, and $R^3$ is as defined below, by a process comprising admixing the compound of Formula F1 with acetonitrile, adding $K_3PO_4$ and water to the mixture, and reacting the mixture containing the compound of Formula F1 under refluxing conditions with a primary amine of the formula $R^3$—$NH_2$, or a salt thereof, wherein $R^3$— is an alkylene-heterocycle.

21. The process of claim 14 further comprising converting the compound of Formula E1 to the compound of Formula F1,

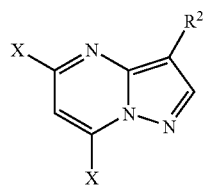

Formula F1 wherein "X" is selected from the group consisting of chloride, bromide, iodide, fluoride and a sulfonyl group having the structure R⁴—SO₂—, and forming therefrom a compound of the structure of Formula Ga5,

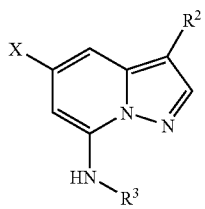

Formula Ga5 wherein, X and R² are as defined above, and R³ is as defined below, by carrying out a first amination on the compound of Formula F1 by a process comprising admixing the compound of Formula F1 with acetonitrile, adding K₃PO₄ and water to the mixture, and reacting the mixture containing the compound of Formula F1 under refluxing conditions with a primary amine of the formula R³—NH₂, or a salt thereof, wherein R³— is an alkylene-heterocycle.

22. The process of claim 20 wherein said mixture is reacted with a primary amine salt of the structure of Formula F1a,

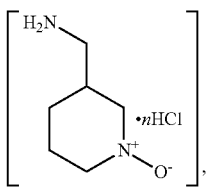

Formula F1a where "n"=1 or 2, thereby forming a compound having the structure of Formula G1a,

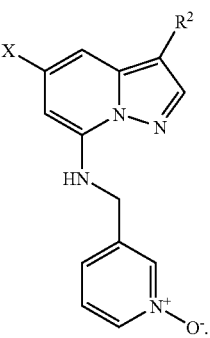

Formula G1a

23. The process of claim 22 wherein, the amount of water added to said reaction mixture is sufficient to provide a volumetric ratio of acetonitrile:water in the reaction mixture of at least about 1:5.

24. The process of claim 20 wherein, the K₃PO₄ and water in the reaction mixture is added to the reaction mixture as a solution.

25. The process of claim 20 wherein, the K₃PO₄ and water in the reaction mixture are added to the reaction mixture separately.

26. The process of claim 20 further comprising aminating the compound of Formula Ga5 at the remaining halogenated carbon to provide a compound of Formula I,

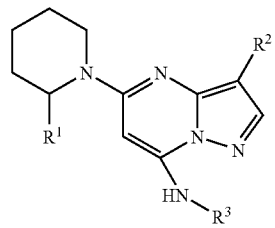

Formula I said process comprising: (i) refluxing the isolated compound of Formula Ga5 in N-methylpyrollidine with a secondary amine in the presence of sodium carbonate and sufficient water to maintain a refluxing temperature of from about 140° C. to about 160° C.; and (ii) optionally isolating the reaction product of Formula I and recyrstallizing it from tetrahydrofuran by adding ethyl acetate.

27. The process of claim 26 wherein, the secondary amine in Step "i" is a compound of the Formula Ha

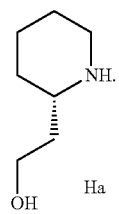

Ha

28. The process of claim 26 wherein optional step (ii) recrystallization is carried out from ethanol by adding tert-butyl methyl ether.

29. A process for making the compound of Formula II,

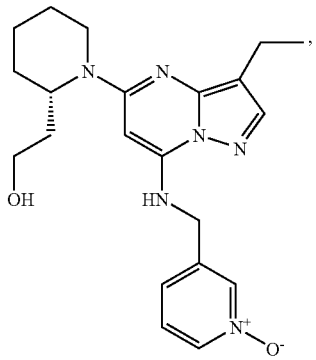

Formula II the process comprising:
a) forming a compound having the structure of Formula E,

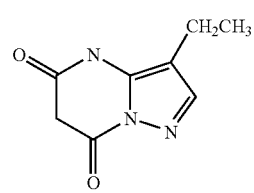

E by reacting, in a refluxing reaction solvent selected from the group consisting of alcohols having 5 or less carbon atoms and mixtures of two or more thereof, a methanol solution of a salt of a 4-alkyl-3-amino-pyrazole compound of Formula C

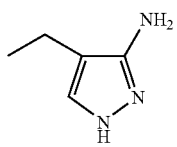

Formula C with a diamidization reagent selected from the group consisting of dimethylmalonate, monomethylmalonylchloride, and malonyl dichloride in the presence of a metal alkoxide base comprising an alkoxide moiety having 5 carbon atoms or less;

b) forming a compound having the structure of Formula F;

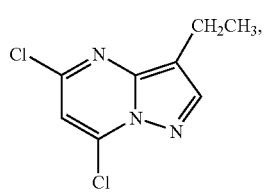

Formula F by reacting the compound of Formula E prepared in Step "a" with phosphorous oxychloride in the presence of a Lewis Base selected from the group consisting of N,N-dimethylaniline, pyridine, diisopropylethylamine, and triethyl amine;

(c) refluxing the reaction mixture from Step "b" containing the compound of Formula F in the presence of a dihydrochloride salt of N-oxide-pyridin-3-yl-amine, K₃PO₄, and water to form the compound of Formula G,

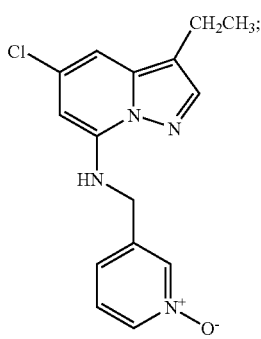

Formula G d) refluxing the isolated compound of Formula G prepared in Step "c" in N-methylpyrollidine in the presence of sodium carbonate, a sufficient water to maintain a refluxing temperature of from about 140° C. to about 160° C., and the amino alcohol compound having the structure of Formula G1a,

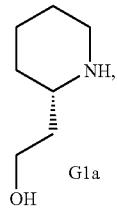

Formula G1a to yield forming the compound of Formula II; and

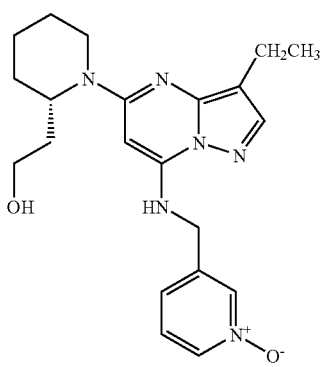

Formula II e) optionally, isolating the compound of Formula II prepared in refluxing Step "d" from the reaction product and recrystalling it from ethanol by adding tert-methyl butyl ether.

30. The process of claim 29 wherein, the amount of water added to the reaction mixture in refluxing Step "d" is sufficient to provide a volumetric ratio of N-methylpyrollidine:water in the reaction mixture of about 100:1.

31. The process of claim 29 wherein, the amount of water added to the reaction mixture in refluxing Step "c" sufficient to provide a volumetric ratio of acetonitrile:water in the reaction mixture of about 1:5.

32. The process of claim 29 wherein, the salt of the compound of Formula C in Step "a" is selected from the group consisting of oxalate, tosylate, and chloride salts.

33. The process of claim 31 wherein the salt of the compound of Formula C in reacting Step "a" is an oxalate salt.

34. The process of claim 31 wherein, the solvent in reacting Step "a" is selected from the group consisting of methanol and ethanol.

35. The process of claim 34 wherein, the metal alkoxide base in reacting Step "a" is selected from the group consisting of sodium methoxide and sodium ethoxide.

36. The process of claim 29 wherein the Lewis base used in Step "b" is selected from the group consisting of N,N-dimethyl aniline, pyridine, diisopropylethylamine, and triethyl amine.

37. The process of claim 36, wherein the Lewis base used in Step "b" is N,N-dimethylaniline.

38. A process for making a pyrazolo[1,5-a]pyrimidin-7-yl-amino compound having the structure of Formula E1,

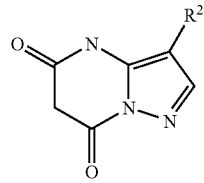

wherein $R^2$ is a linear, branched or cyclic alkyl group, the process comprising reacting, in a refluxing reaction solvent selected from the group consisting of alcohols having 5 or less carbon atoms and mixtures of two or more thereof, a methanol solution of a salt of a 4-alkyl-3-amino-pyrazole compound of Formula C1

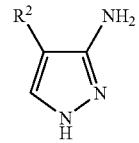

with a diamidization reagent selected from dimethylmalonate, monomethylmalonylchloride, and malonyl dichloride in the presence of a Lewis base having sufficient proton affinity to abstract a proton from the 1-position nitrogen present in the pyrazole ring.

39. The process of claim 38, wherein the salt of the compound of Formula C1 is an oxalate salt.

40. The process of claim 38, wherein $R^2$ is a linear alkyl of 4 carbons or less.

41. The process of claim 40, wherein $R^2$ is ethyl (—$CH_2$—$CH_3$).

* * * * *